(12) United States Patent
Patton et al.

(10) Patent No.: US 7,540,284 B2
(45) Date of Patent: Jun. 2, 2009

(54) POWDER AEROSOLIZATION APPARATUS AND METHOD

(75) Inventors: John S. Patton, Portola Valley, CA (US); Michael T. Newhouse, Foster City, CA (US)

(73) Assignee: Novartis Pharma AG, Basel (CH)

( * ) Notice: Subject to any disclaimer, the term of this patent is extended or adjusted under 35 U.S.C. 154(b) by 1125 days.

(21) Appl. No.: 10/175,145

(22) Filed: Jun. 19, 2002

(65) Prior Publication Data

US 2003/0035777 A1    Feb. 20, 2003

Related U.S. Application Data

(60) Provisional application No. 60/299,694, filed on Jun. 20, 2001.

(51) Int. Cl.
  A61M 15/00 (2006.01)
  A61M 16/00 (2006.01)
  A61M 15/08 (2006.01)

(52) U.S. Cl. .................. 128/203.12; 128/203.13; 128/203.14; 128/203.15; 128/203.18; 128/203.21; 128/203.22

(58) Field of Classification Search ............ 128/203.12–203.23
See application file for complete search history.

(56) References Cited

U.S. PATENT DOCUMENTS

| | | | |
|---|---|---|---|
| 4,043,478 A * | 8/1977 | Duncan | 220/710 |
| 5,722,561 A * | 3/1998 | Biondich et al. | 220/710 |
| 5,740,794 A * | 4/1998 | Smith et al. | 128/203.15 |
| 5,785,049 A | 7/1998 | Smith et al. | |
| 5,826,663 A | 10/1998 | Sundholm | |
| 5,865,012 A | 2/1999 | Hansson et al. | |
| 5,922,675 A | 7/1999 | Baker et al. | |
| 6,182,712 B1 | 2/2001 | Stout et al. | |
| 6,257,233 B1 | 7/2001 | Burr et al. | |
| 6,809,228 B2 | 10/2004 | Ducreux et al. | |

FOREIGN PATENT DOCUMENTS

| | | |
|---|---|---|
| WO | 95/24183 | 9/1995 |
| WO | 96/32096 | 10/1996 |
| WO | 96/32149 | 10/1996 |
| WO | 99/16419 | 4/1999 |
| WO | 99/16422 | 4/1999 |

OTHER PUBLICATIONS

U.S. Appl. No. 09/731,318, filed Dec. 6, 2000, Paboojian et al.

* cited by examiner

*Primary Examiner*—Shengjun Wang
(74) *Attorney, Agent, or Firm*—Naishadh Desai; Guy Tucker (57) ABSTRACT

An aerosolization device comprises a chamber adapted to contain a powder pharmaceutical formulation, a lid at least partially covering the chamber, at least one piercing element forcible through the lid to provide access to the powder pharmaceutical formulation, and a shapeable surface extending from the chamber, the shapeable surface being adapted to undergo a shape change to form a conduit. The powder pharmaceutical formulation may be extracted from the chamber by a user inhaling through the conduit. In another version, the lid is removable from the chamber without the need for a piercing element.

17 Claims, 7 Drawing Sheets

POWDER AEROSOLIZATION APPARATUS AND METHOD

This application claims priority to U.S. Provisional Application Ser. No. 60/299,694 filed Jun. 20, 2001.

BACKGROUND OF THE INVENTION

This invention relates generally to the field of aerosolizing a powder pharmaceutical formulation, such as a dry powder drug and/or vaccine.

The need for effective therapeutic treatment of patients has resulted in the development of a variety of techniques for delivering a pharmaceutical formulation to a patient. Traditional techniques for delivering a pharmaceutical formulation involve, needle injection and oral delivery in the form of a pill, capsule, or the like. Inhaleable drug delivery, where an aerosolized pharmaceutical formulation is orally or nasally inhaled by a patient to deliver the formulation to the patient's respiratory tract, has also proven to be an effective manner of delivery. In one inhalation technique, a pharmaceutical formulation is delivered deep within a patient's lungs where it may be absorbed into the blood stream. Many types of inhalation devices exist including devices that aerosolize a dry powder pharmaceutical formulation. However, these devices are often cumbersome and/or are difficult or costly to manufacture and/or are inadequate at delivering the pharmaceutical formulation.

Pulmonary delivery has been shown to be a particularly promising pharmaceutical formulation delivery technique for certain therapies. For example, the delivery of proteins and polypeptides, which can be difficult to deliver by other routes of administration, can be effectively delivered by inhalation. Such pulmonary delivery is effective both for systemic delivery and for localized delivery to treat diseases of the lungs. In addition, pulmonary delivery of some vaccines has been shown to be more effective than needle injection. This is believed to be due to this technique conferring mucosal as well as systemic immunity. For example, inhaled measles vaccines have been successfully administered to millions of Mexican and thousands of South African children safely and more effectively than injected vaccines.

Therefore, it is desirable to be able to offer the benefits of pulmonary delivery without the need of a cumbersome, expensive, and/or inefficient device. It is further desirable to be able to provide an aerosolization device that is simple and efficient to make and/or operate.

SUMMARY

The present invention satisfies these needs. In one aspect of the invention an aerosolization device comprises a chamber adapted to contain a powder pharmaceutical formulation, a lid at least partially covering the chamber, at least one piercing element forcible through the lid to provide access to the powder pharmaceutical formulation, and a shapeable surface extending from the chamber, the shapeable surface being adapted to undergo a shape change to form a conduit, whereby the powder pharmaceutical formulation may be extracted from the chamber by a user inhaling through the conduit.

In another aspect of the invention, an aerosolization device comprises a chamber adapted to contain a powder pharmaceutical formulation, a lid at least partially covering the chamber, and at least one piercing element connected to the chamber, the piercing element being forcible through the lid to provide access to the powder pharmaceutical formulation, whereby the powder pharmaceutical formulation may be extracted from the chamber by a user inhaling in proximity to the chamber.

In another aspect of the invention, an aerosolization device for aerosolizing a powder pharmaceutical formulation contained within a chamber having a lid comprises a shapeable surface adapted to undergo a shape change to form a conduit, and at least one piercing element connected to the shapeable surface, the piercing element being positioned so that is may be forced through the lid to provide access to the powder pharmaceutical formulation, whereby the powder pharmaceutical formulation may be extracted from the chamber by a user inhaling through the conduit.

In another aspect of the invention, a method of aerosolizing a pharmaceutical formulation comprises providing a chamber containing a powder pharmaceutical formulation at least partially covered by a puncturable lid, providing a surface that is shapeable into the form of a conduit, and after the lid is punctured, aerosolizing the powder pharmaceutical formulation in response to a user inhaling through the conduit.

In another aspect of the invention, a method of aerosolizing a pharmaceutical formulation comprises shaping a shapeable surface into the form of a conduit, puncturing the lid of a chamber containing a powder pharmaceutical formulation, and inhaling through the conduit to aerosolize the pharmaceutical formulation.

In another aspect of the invention, a method of aerosolizing a pharmaceutical formulation comprises puncturing the lid of a chamber containing a powder pharmaceutical formulation, wherein the puncturing is performed with a piercing element attached to the chamber, and inhaling through a conduit to aerosolize the pharmaceutical formulation.

In another aspect of the invention, a method of making an aerosolization apparatus comprises providing a surface, forming one or more perforations in the surface so that the surface may be shaped into the form of a conduit, and forming a member in the surface whereby a pharmaceutical formulation may be positioned in proximity to the conduit.

In another aspect of the invention, a method of making an aerosolization apparatus comprises providing a surface, forming a chamber in the surface and providing a powder pharmaceutical formulation within the chamber, and forming at least one piercing element in the surface with which the powder pharmaceutical formulation may be accessed.

In another aspect of the invention, an aerosolization device comprises a chamber adapted to contain a powder pharmaceutical formulation, a lid removably covering at least a portion of the chamber, and a shapeable surface extending from the chamber, the shapeable surface being adapted to undergo a shape change to form a conduit, whereby the powder pharmaceutical formulation may be extracted from the chamber by a user inhaling through the conduit.

According to one embodiment of the invention, an inhalation device comprises a chamber containing a unit dosage of a powdered medicament that is covered by a pierceable lid. A bendable surface extends from the chamber and contains at least one piercing element. The bendable surface may be manually shaped to form a conduit through which the medicament is extracted during inhalation through the conduit. The piercing element is operably coupled to the chamber in such a configuration that the lid covering the chamber is forcibly pierced by the element when the bendable surface is manually shaped to form the conduit for inhalation, when the element is squeezed through the lid, or the like.

In another embodiment, an inhalation device comprises a device body having a conduit region defining a conduit and a storage region having a chamber containing a unit dosage of a powdered medicament that is covered by a pierceable lid. At least one piercing element is operably coupled to the device body and is configured to be forced through the lid to provide access to the medicament. In this way, the medicament is extractable from the chamber by inhaling through the conduit. Conveniently, the conduit may be formed at the time of manufacture, such as by using a machine to roll the device body into the conduit after the device body has been stamped from a sheet of material. Alternatively, the device body may be rolled into a conduit by the user prior to inhalation.

This invention also provides techniques for forming an aerosolization device as well as for aerosolizing a powdered medicament. The aerosolization device in one embodiment is formed from a receptacle comprising a bendable surface, at least one piercing element, and a chamber with a pierceable lid. The piercing element is employed to gain access to the powder by piercing the lid, and the bendable surface is manipulated to form a conduit. A user inhales through the conduit to extract the powder from the chamber and entrain the powder in the gas stream produced by the user. Hence, a relatively simple and inexpensive way is provided to administer a unit dose of a medicament to a patient utilizing the same receptacle used to store the medicament.

In some embodiments, the aerosolization device may be separate from a receptacle containing the powder. In this way, the aerosolization device may be reused with different receptacles, while still being relatively simple and inexpensive. For example, one such an inhalation device comprises a device body having a conduit region defining a conduit and a holding region that is adapted to hold a receptacle having a chamber containing a unit dosage of a powdered medicament that is covered by a pierceable lid. At least one piercing element is operably coupled to the device body and is configured to be forced through the lid to provide access to the medicament. In this way, a user may simply insert the receptacle into the holding region of the device, force the piercing element through the lid, and then inhale through the conduit to extract and aerosolize the medicament.

In one aspect, the holding region includes a depression for receiving the chamber of the receptacle. In this way, the receptacle is held in place while being opened and during aerosolization.

Such an aerosolization device may incorporate many of the features of the aerosolization devices having an integrated chamber as previously described, and vice versa. For example, the conduit region may comprise a sheet of material that is fashioned to form the conduit. This may be done at the time of manufacture, or by the user. Further, the device body may conveniently be formed from a stamping process. As another example, the piercing element may be spaced apart from the conduit to facilitate squeezing of the piercing element through the lid. As a further example, another piercing element is operably coupled to the device body, such as on an opposite side of the chamber. In this way, more than one hole may be provided in the lid. The piercing element may also have a variety of shapes and sizes, such as having a single point, multiple points, curves, and flat.

In one particular aspect, any of the devices may be configured such that the piercing element stops penetration at a known distance so that the size of the opening is consistent with each operation. This may be accomplished by providing the user with tactile feedback when the proper penetration has been achieved. For example, the piercing element may be configured to be forced through the lid until the piercing element contacts a bottom of the chamber. Further, the piercing element may be configured to spring back out of the chamber when released to leave the hole fully open. This may be accomplished by constructing the piercing element of a resilient material that returns to its initial shape after being squeezed.

DRAWINGS

These features, aspects, and advantages of the present invention will become better understood with regard to the following description, appended claims, and accompanying drawings which illustrate exemplary features of the invention. However, it is to be understood that each of the features can be used in the invention in general, not merely in the context of the particular drawings, and the invention includes any combination of these features, where:

DESCRIPTION

The present invention relates to the aerosolization of a pharmaceutical formulation, such as a drug and/or vaccine. Although the process is illustrated in the context of delivering a dry powder pharmaceutical formulation, the present invention can be used in other processes and should not be limited to the examples provided herein.

The present invention provides, for example, simple and easy ways to deliver a pharmaceutical formulation, such as a dry powder drug and/or vaccines in a simple, inexpensive and efficient manner. The apparatus and methods disclosed are particularly useful in delivering unit dosages via inhalation administration routes, such as through the mouth, the nose, and the like. According to one embodiment of the invention, pulmonary delivery may be achieved by creating an aerosolization device out of a receptacle used to store the powder. The aerosolization device may be adapted to aerosolize the pharmaceutical formulation as a user inhales. In this way, a user may be provided with a relatively inexpensive receptacle that contains a unit dose of a dry powder, convert the receptacle into an inhalation device, and inhale the powder to deliver the dose. In some cases, the receptacle may be fashioned into the shape of an inhaler at the time of manufacture so that all the user needs to do is to open the chamber and then inhale through the device. In other cases, the shaping may be performed by the user just before inhaling through the device.

As one example, an aerosolization device having an integrated receptacle may comprise a device body having a conduit region defining a conduit and a storage region having a chamber containing a unit dosage, or other amount, of a powdered pharmaceutical formulation that is covered by a lid, such as a pierceable lid. At least one piercing element may be operably coupled to the device body and is configured to be forced through the lid to provide access to the medicament. Subsequently, the user may inhale through the conduit to extract and aerosolize the powder. Hence, with such a configuration, the user may easily form an aersolization device out of a receptacle, pierce the receptacle and then inhale to receive the medicament.

In another embodiment, an aerosolization device may be used with separate receptacles, and may include many of the same features as the aerosolization device having an integrated receptacle. In this version, the aerslization device may be reused while still being simple to use and relatively inexpensive. Aeroslization devices using a separate receptacle may comprise a device body having a conduit region defining a conduit and a holding region for holding a receptacle having a chamber containing a unit dosage of a powdered medicament that is covered by a pierceable lid. At least one piercing element is operably coupled to the device body and is configured to be forced through the lid to provide access to the medicament. With such a configuration, the user simply needs to insert the receptacle, pierce the lid, and then inhale through the conduit to extract and aerosolize the medicament.

Hence, the inhalation devices of the invention, whether including an integrated receptacle or not, may have a variety of features in common. For example, they both may be fabricated to pre-form the conduit, or come as a sheet where the user forms the conduit. As another example, the inhalation devices may include similar piercing elements, conduit designs, and the like. Also the receptacle chambers may have similar sizes and shapes.

The invention may utilize a variety of receptacles that may be converted into an aerosolization device or be used with a separate aerosolization device. Such receptacles may have a cavity or chamber having a sealed unit dose of powder. The sealed chamber protects the powder from the environment and increases its shelf life. The chamber is connected to some type of material that can be manipulated to form a conduit that passes over the chamber. In this way, the unit dose of powder may be packaged and shipped in the form of a receptacle in a relatively inexpensive manner. When ready to receive the dose, the user simply opens the cavity, forms the conduit (if needed), and inhales through the conduit to extract the powder in a gas stream created by the inhalation. As the user continues to inhale, the aerosolized powder flows to the user's lungs. Alternatively, such receptacles may simply be placed into a separate inhalation device which is used to pierce the lid in a similar manner.

In one version, the aerosolization device may comprise or accommodate a receptacle that may be used to store a pharmaceutical formulation, such as a "blister package" type of receptacle where a "blister" or cavity is formed in a piece of material and a lid or seal is placed over the cavity to seal the powder within the cavity. Examples of such receptacles are described in U.S. Pat. Nos. 5,785,049; 5,740,794; 5,865,012, and 6,809,228 and in copending U.S. application Ser. No. 09/312,434, filed May 14, 1999; and Ser. No. 09/731,318, filed Dec. 6, 2000, the disclosures of all of which being incorporated herein by reference in their entireties. One advantage of modifying a blister package into an aerosolization device is that commercially available equipment and known techniques may be used to form and fill such receptacles in a cost efficient manner. Such receptacles may also be formed and filled in a high throughput manner. For instance, techniques for filling such receptacles are described in U.S. Pat. Nos. 5,826,663 and 6,182,712, both of which are incorporated herein by reference in their entireties.

The aerosolization device of the invention may be constructed of a wide variety of materials. For example, the device may be formed from any type of material that may be stamped to form the cavity. Molded materials may also be used to form the cavity or any other portion of the device. The materials should also be conducive with the type of contained pharmaceutical formulation. Examples of materials that may be used include those described in the above cited patents and patent applications. The shapeable or bendable material that is used to form the conduit may comprise essentially any type of deformable material that will hold its shape, including metals, such as aluminum, and stainless steel, paper products, and the like. Further, the piercing elements may be formed from a material with spring-link characteristics so that they move back to their original position after being inserted into the cavity. In this way, the piercing elements will not interfere with the aerosolization and delivery process.

One convenient way to construct the receptacle is by using a metal bottom that has a stamped cavity so that one or more edges extend from the cavity. A foil covering may be sealed over the cavity to seal the powder. The edges may then be bent or rolled to form the conduit. The formation of the conduit may be done at the time of manufacture using equipment designed to roll the edges into the shape of a conduit. Alternatively, the conduit may be formed by the user, thereby further reducing the cost of the inhalation device.

To provide access to the pharmaceutical formulation, a variety of techniques may be used. For example, one way to gain access to the pharmaceutical formulation is by piercing the chamber at one or more locations. When the chamber is covered by a pierceable lid, access to the powder may be gained by using a pointed or sharpened surface that pierces the lid. For example, one or more pointed tabs may be used to pierce or cut the lid. These may be operably connected to the chamber so that the lid may be pierced simply by manipulating the tab so that its pointed end faces the lid and then forcing the tab through the lid. For example, the user may simply place the device between the thumb and forefinger and squeeze the tab through the lid. Conveniently, the piercing tabs may be cut from the edges of the receptacle that are used to form the conduit. With this configuration, the tabs may be bent and pushed into the lid to pierce the foil prior to forming the conduit. As another example, the receptacle may include an opening tool that is removable so that the user may remove the tool from the receptacle and then pierce or remove the lid. For instance, the tool may comprise a portion of the receptacle that is held in place by tabs separated by score lines. In this way, the tool may be torn from the receptacle prior to use. As another option, an opening tool may be provided along with the packaging used to store the receptacle.

The number and size of openings formed in the cavity may vary depending on the application and the type of powder. For example, a single opening or a plurality of openings could be formed of a size suitable to accommodate sufficient airflow to disperse and aerosolize the powder. Optionally, one or more vent openings may also be formed. The openings are formed in locations which are tangential to the gas stream flowing through the conduit so that the flowing gas stream may draw the powder out of the cavity due to a venturi effect.

A variety of techniques may be used to form the conduit. For example, the cavity may be located along a central axis of the receptacle so that opposing edges of the receptacle may be rolled or bent until they touch each other or overlap to form the conduit. Alternatively, the cavity may be offset toward one side so that only one side needs to be bent or rolled to form the cavity. The conduit may have a cross sectional area of about 0.5 mm to about 3 mm. Further, the cross sectional area of the conduit may vary along its length. For example, the conduit may have a smaller opening nearest the chamber. The length of the conduit may be in the range from about 2.5 cm to about 10 cm. In one aspect, the conduit may be preformed by a packaging machine and the piercing elements positioned close to and directly above the chamber so that a simple squeeze of the wings between the thumb and fore finger will pierce the lid and open the chamber.

A gas stream flowing through the conduit may be generated by the user by inhaling at one end of the conduit. The gas stream may be sufficient to aerosolize the pharmaceutical formulation in the chamber. For example, flow rates that may be generated to extract a powder may be in the range from about 10 L/min to about 90 L/min. In this version, the pharmaceutical formulation may be inhaled orally or through the nose.

A wide variety of pharmaceutical formulations powders may be aerosolized using the techniques of the invention. Examples of drugs and vaccines that may be aerosolized include antibiotics, antibodies, antiviral agents, antiepileptics, and bronchodilators, and viruses and may be inorganic and organic compounds, including, without limitation, drugs which act on the peripheral nerves, adrenergic receptors, cholinergic receptors, the skeletal muscles, the cardiovascular system, smooth muscles, the blood circulatory system, synaptic sites, neuroeffector junctional sites, endocrine and hormone systems, the immunological system, the reproductive system, the skeletal system, autacoid systems, the alimentary and excretory systems, the histamine system and the central nervous system, and the like. The powders may have a particle size in the range from about 0.5 µm to about 10 µm, and more preferably from about 0.5 µm to about 5 µm. For some cases, such as for nasal or buccal deposition, the particles sizes may be in the range from about 10 µm to about 50 µm. The chamber in the receptacle may be configured to hold unit dosages in the range from about 0.5 mg to about 50 mg. The invention will find one particular use with drugs or vaccines where variability in the delivered dose is permissible. Such variability may occur if some powder remains in the chamber after inhalation. In such cases extra powder may be stored in the chamber.

Hence, in one advantageous use of the present invention, large populations may be vaccinated in a simple and efficient manner, without the risk of cross contamination with infectious agents. The aerosolization devices of the invention provide for the administration of unit dosages, or other amounts, and in some embodiments the drug carrier unit and the aerosolization device are integrated with each other so that the device is inexpensive and may be discarded after the unit dose has been inhaled. The aerosolization devices may also be relatively small and light weight so that they may be easily shipped and stored. They are easy to assembly and operate so that they may be used by a wide variety of patients.

Figure 1:
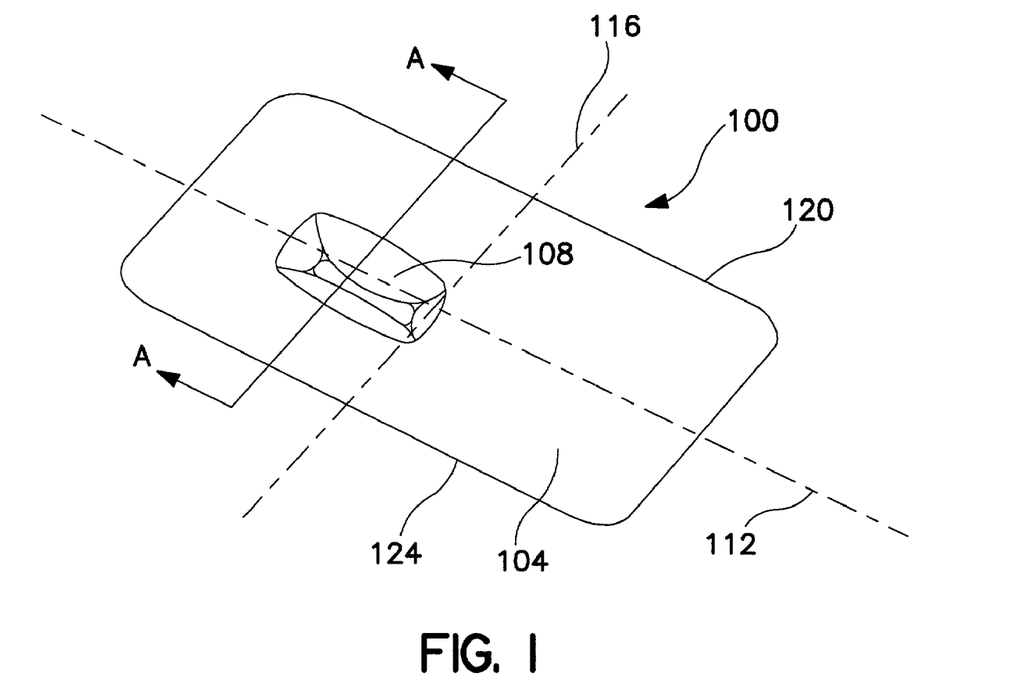
FIG. 1 is a schematic bottom perspective view of an aerosolization device of the invention.

Referring to FIG. 1, a bottom view of an embodiment of an aerosolization device 100 is shown. The aerosolization device 100 comprises at least one shapeable portion 102. In this version of FIG. 1, the shapeable portion 102 comprises a bendable receptacle material 104, like plastic or metal, whose overall shape may, for example, be that of a rectangle, with the two longer sides having edges 120 and edge 124. This bendable receptacle material 104 is in a sufficient gauge or thickness that can be bent, molded, formed and/or rolled into a desired shape. The bendable receptacle material 104 includes or is connected to a dosage chamber 108 that protrudes out the bottom side of the flat sheet. Conveniently, any shape and size of the dosing chamber 108 can be utilized as long as it is suitable for holding the contents of a given pharmaceutical formulation, such as a dry powder pharmaceutical formulation. In the version shown, the placement of the dosing chamber 108 is symmetrical across a longitudinal central axis 112 of the bendable receptacle material 104. In this way, its centroid lies on the central axis 112 and to one side of a minor axis 116. Other embodiments could have the placement of the centroid of the dosing chamber 108 anywhere along the entire longitudinal central axis 112. The shapeable portion 102 may be the entire aerosolization device or just a portion thereof, and there may be more than one shapeable portions. The shapeable portion 102 may be designed to be shaped by a subsequent manufacturing process or may be designed to be shaped by a user of the device during or just before usage.

Figure 2:
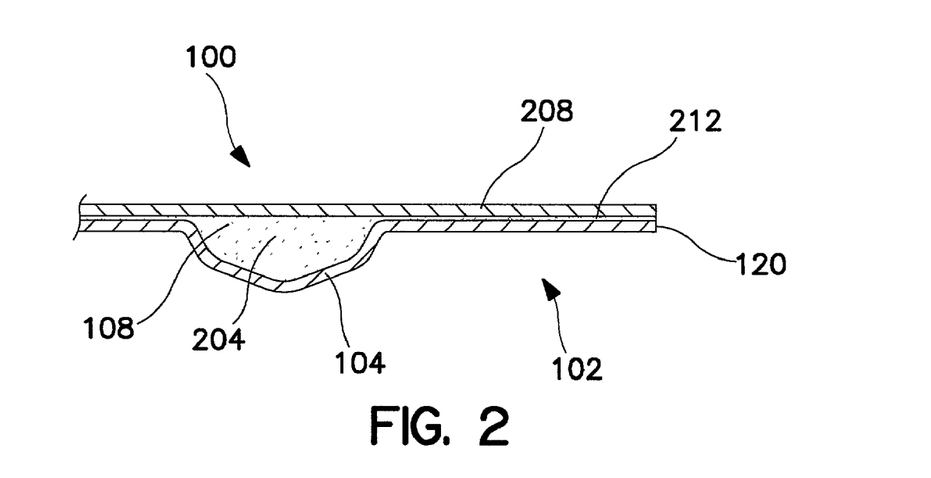
FIG. 2 is a schematic sectional side view of the aerosolization device of FIG. 1.

The dosing chamber 108 may be formed by the joining of the bendable receptacle material 104 to a lid covering material 208 in order to encapsulate a dry powder dosage 204, as shown in the sectional view of the aerosolization device 100 of FIG. 2. A bonding joint 212 exists between the two joined materials 104, 208. Joint 212 may be an adhesive substance such as glue, a bonding film such as double sided tape, a layer that results from the manufacturing process of which may include chemical reactions and heat bonds, or the like. The bonding joint 212 is formed in such a fashion that any additional treatment of edge 120 is possible.

Figure 3:
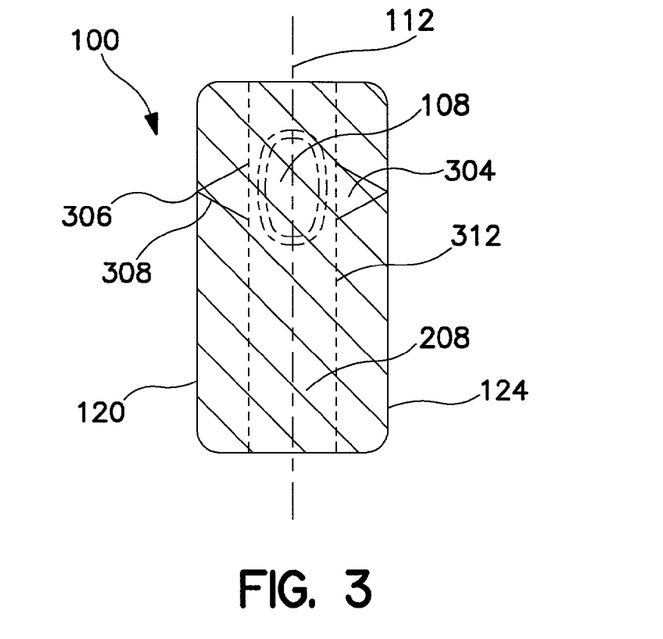
FIG. 3 is a schematic top view of a version of an aerosolization device.

The aerosolization device 100 may comprise one or more means for encouraging the shapeable portion into a desired shape. For example, as shown in the version of FIG. 3, one or more perforations may be cut through the lid covering material 208 and/or the bendable receptacle material 104. A rolling perforation 312 may be included as a series of longitudinal cuts in a dashed line fashion that are cut through the two joined materials 104, 208. Rolling perforations 308 may be used to weaken the bendable material's rigidity in such a manner that the two joined materials 104, 208 can be more easily rolled into a conduit, such as a tube-like shape. Alternatively other means for encouraging the shapeable portion into a desired shape may be included. For example, the shapeable portion may be composed of shape memory material or may be biased into a desired configuration.

Additionally or alternatively, one or more perforations may be provided to define one or more piercing elements. For example, as shown in FIG. 3, a piercing element perforation 308 is provided in the form of a perforation line that is cut through the two joined materials 104, 208 in two places. When separated along perforations 308, a piercing element 304 with a piercing point 306 is formed. In this version, the piercing element perforations 308 form the piercing element 304 by joining two perforations of the same length at a single endpoint. The piercing element 304 that results is in the shape of a triangle with two sides being formed by two piercing element perforations 308 and one side remaining attached to one or both of the two joined materials 104, 208. The piercing point 306 is designed to penetrate the lid covering material 208 of dosing chamber 108 and allow for the extraction of the dry powder dosage 204.

Two piercing elements 304 are shown in the embodiment of FIG. 3, one on each side of the dosing chamber 108 and symmetrical to the longitudinal central axis 112. Similarly, two rolling perforations 312 are cut longitudinally into the convertible storage receptacle 100 and symmetrical to the longitudinal central axis 112 to help the user roll the two joined materials 104, 208 into a conduit or a tube-like shape. Alternatively, the rolling perforations 312 may not extend only along a portion of the length of the aerosolization device 100. For example, the rolling perforations 312 may extend from the end of the device which is to be engaged by the user and may terminate just before the piercing elements so that only the portion downstream of the chamber 108 is shaped. A cut from the edges 120, 124 to the rolling perforations 312 may be provided to facilitate this shaping of the downstream portion. Depending on the types of materials 104, 208 used, it may not be necessary to use any rolling perforations 312.

Figure 4:
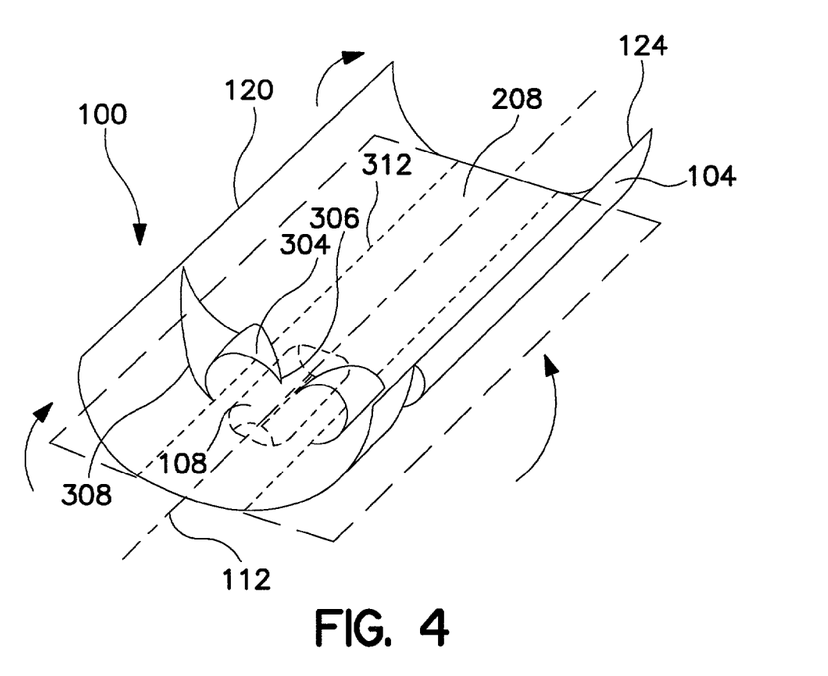
FIG. 4 is a schematic perspective view of the aerosolization device of FIG. 3 being converted into a aerosolization configuration.

Referring to FIG. 4, an isometric view of aerosolization device 100 is shown being converted into a ready to use form. This view illustrates how the process of rolling the two joined materials 104, 208 forms a conduit for inhalation by the user. FIG. 4 also illustrates how the piercing elements 304 can be rolled separately from the leading edges 120, 124 to penetrate lid covering material 208 and access the contents of dosing chamber 108. Conveniently, the conduit may be formed by rolling edge 120 of the two joined materials 104, 208 in a direction rotating clockwise from the longitudinal central axis 112, and by rolling edge 124 of the two joined materials 104, 208 in a direction rotating counter clockwise from the longitudinal central axis 112.

Figure 5:
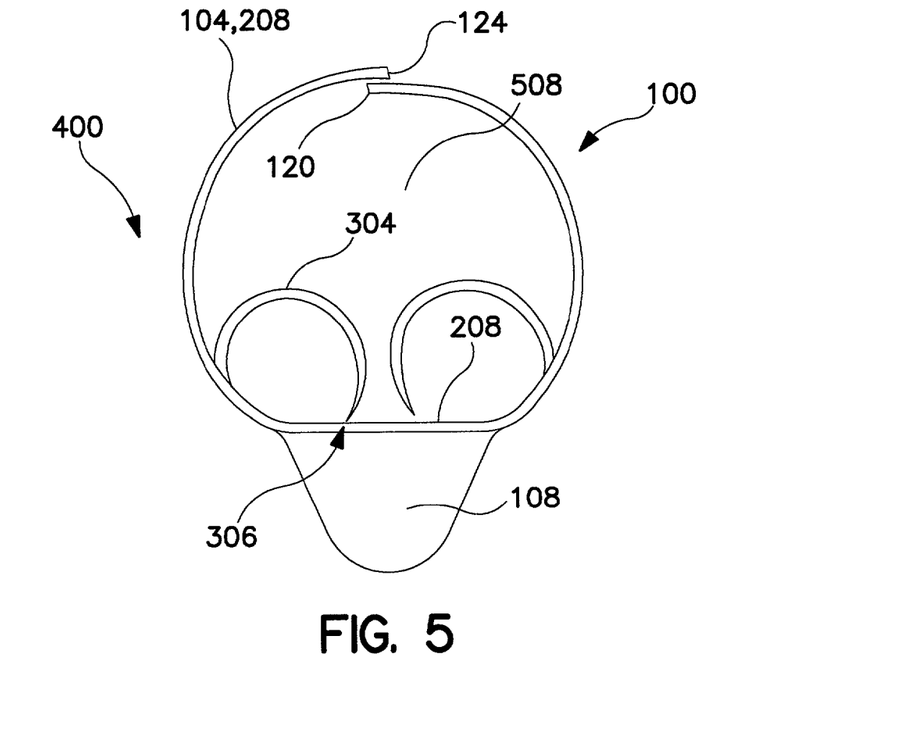
FIG. 5 is a schematic end view of the aerosolization device of FIG. 3 after being converted into the aerosolization configuration.

To provide access to dosing chamber 108, the piercing elements may be separated from leading edges 120, 124 at the piercing element perforations 308 and rolled in a tight enough arc such that the piercing point can penetrate the lid covering material 208. Alternatively, the partially-rolled piercing elements 304 may be squeezed using fingertips or some other mechanism until penetration of the lid covering material 208 by the piercing elements 304 is achieved. When releasing piercing elements 304, they preferably spring back out of chamber 108, leaving holes in the lid to permit the powder to be extracted. FIG. 5 shows an end view of aerosolization device in its ready to use configuration 400 after piercing elements 304 have formed access holes and after the conduit has been formed.

Figure 6:
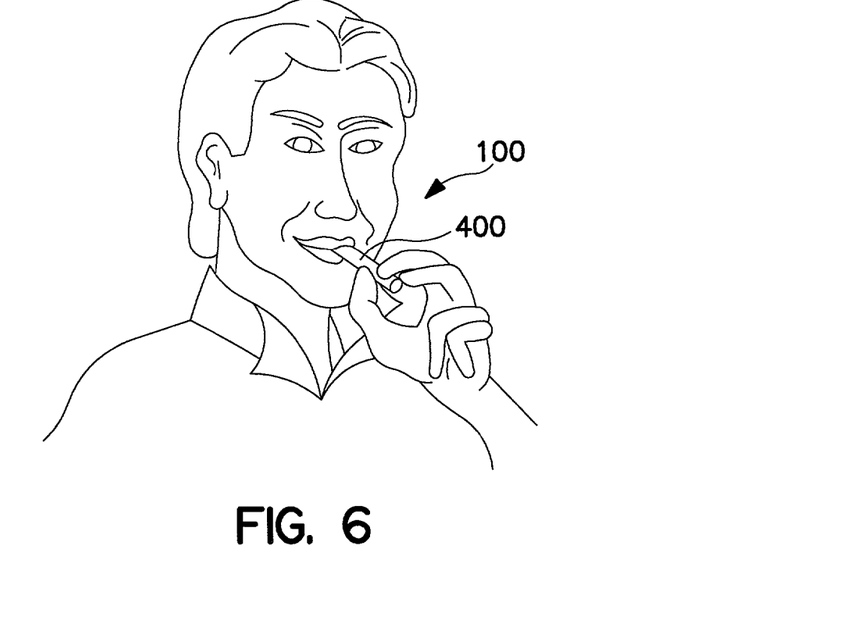
FIG. 6 is an illustration of the aerosolization device of FIGS. 3-5 in use.

Referring to FIG. 6, aerosolization device 100 is shown in use in its aerosolization configuration 400. After piercing elements 304 have formed access holes into dosing chamber 108 and the two joined materials 104, 208 have been rolled to form conduit 508, the user holds the inhaler device 400 between the lips and inhales. The flow of air across the opening of the chamber 108 draws the powder pharmaceutical formulation out of the chamber and aerosolizes the powder so that it may be inhaled by the user. In addition, the aerosolization device 100 may be designed so that a portion of the flowing gas passes through the chamber to collect the pharmaceutical formulation and/or so that a venturi is formed that assists in drawing the pharmaceutical formulation out of the chamber.

Figures 7, 9:
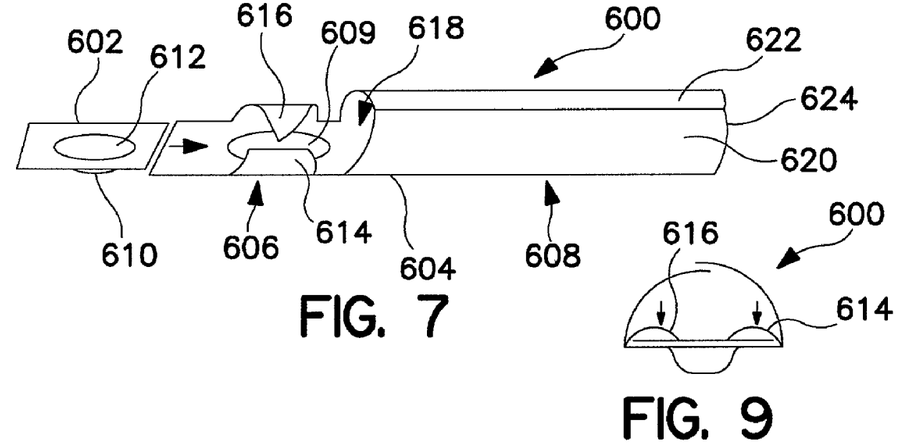
FIG. 7 is a schematic perspective view of another version of an aerosolization device.
FIG. 9 is a schematic end view of the aerosolization device of FIG. 7 holding a receptacle.

FIG. 7 illustrates a version an aerosolization device 600 on which a separate receptacle 602 may be removably positioned. However, it will be appreciated that receptacle 602 could be incorporated into inhalation device 600 in a manner similar to other embodiments. Device 600 comprises a device body 604 having a holding region 606 and a conduit region 608. Holding region 606 includes a depression 609 that is configured to receive receptacle 602. More specifically, receptacle 602 includes a chamber 610 that is covered by a pierceable lid 612 and includes an amount of a powdered medicament that is to be inhaled. Receptacle 602 is inserted into holding region 606 as indicated by the arrow until chamber 610 rests within depression 609 of holding region 606. In another version, the depression 609 may be replaced by an opening shaped to receive the chamber 610.

Figure 8:
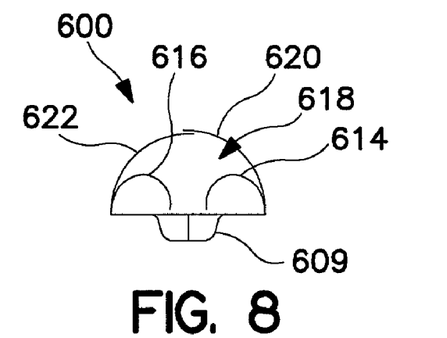
FIG. 8 is a schematic end view of the aerosolization device of FIG. 7.

Device body 604 further includes a pair of piercing elements 614 and 616 that are conveniently disposed on either side of depression 609. As best shown in FIG. 8, piercing elements 614 and 616 are positioned over holding region 606 so that they may be squeezed to penetrate lid 612. Such a process is illustrated in FIG. 9 where the arrows represent the direction of movement of piercing elements 614 and 616. Piercing elements 614 and 616 are constructed of a material that permits them to spring back to the position shown in FIG. 8 after lid 612 has been pierced. In this way, piercing elements 614 and 616 will not interfere with the aerosolization process. One convenient way to force piercing elements 614 and 616 through lid 612 by grasping holding region 606 between the user's forefinger and thumb and then squeezing to force piercing elements 614 and 616 through lid 612.

The user may further be provided with instructions as to the depth of penetration of piercing elements 614 and 616 so that holes of consistent size may be repeatedly produced each time device 600 is operated. For example, the user may be instructed to depress piercing elements 614 and 616 until the user feels them contact the bottom of chamber 610. Alternatively, elements 614 and 616 could be provided with markers, tabs, detents, or the like that indicate when piercing elements 614 and 616 have been depressed to the proper depth.

Conduit region 608 defines a conduit 618 that is formed from rolling two sides 620 and 622 of device body 604 into the shape shown. Conduit 618 may conveniently formed at the time of manufacture or rolled into the shape shown by the user when ready to receive a medication. Sides 620 and 622 are preferably constructed of a material that will hold its shape so that conduit 618 may maintain its shape for extended periods.

After receptacle 602 has been inserted into holding region 606 and holes have been formed in lid 612, the user places his mouth over an end 624 of device 600 and inhales. In so doing, a gas stream is created through conduit 618 and passes over lid 612. In so doing, the powder is extracted from chamber 610 and is drawn into the flowing gas stream where it is aerosolized and delivered through end 624 to the patient, as discussed above.

Figure 10:
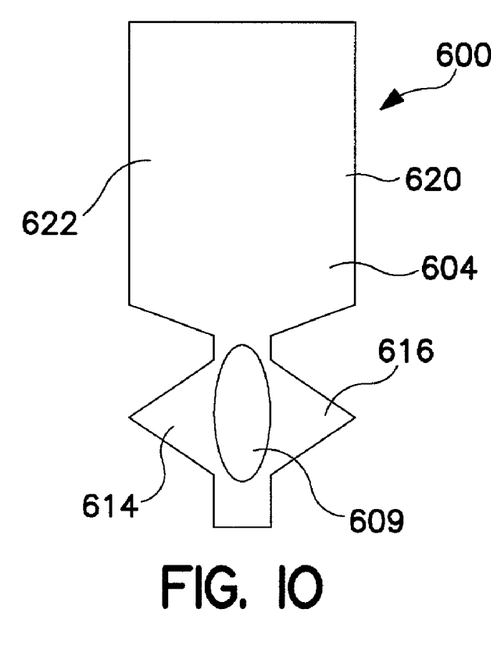
FIG. 10 is a schematic top view of the aerosolization device of FIG. 7 before it is converted into its aerosolization configuration.

FIG. 10 illustrates device 600 prior to being fashioned into the shape shown in FIG. 7. FIG. 10 is provided to illustrate that device 600 may be conveniently formed by stamping device body 604 from a sheet of material, with the stamping process also forming depression 609. Sides 620 and 622 may then be rolled to form conduit 618. Similarly, piercing elements 614 and 616 may be bent so as to be positioned over depression 609 as shown in FIG. 7.

Figure 11:
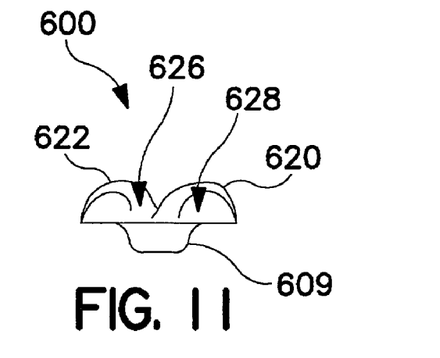
FIG. 11 is a schematic end view of another version of the aerosolization device.
Figure 12:
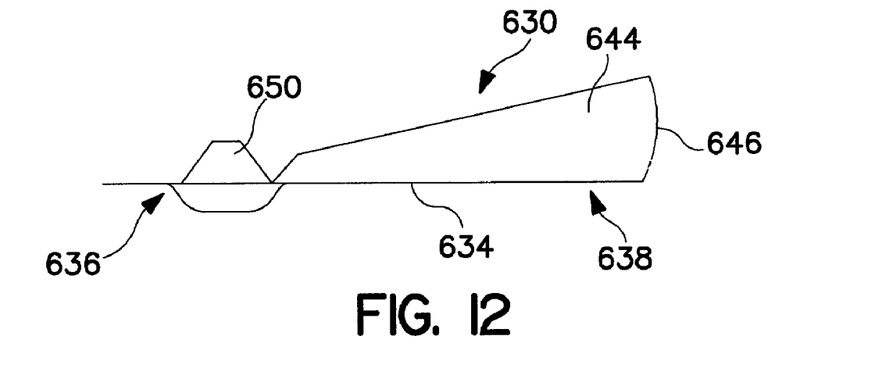
FIG. 12 is a schematic side view of another version of an aerosolization device.
Figure 13:
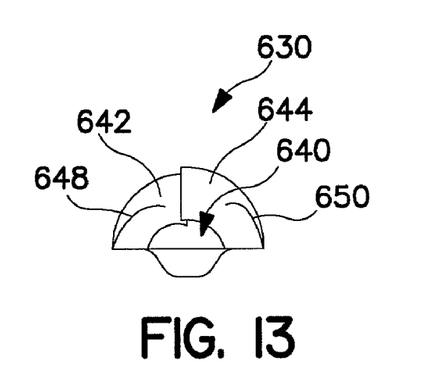
FIG. 13 is a schematic end view of the aerosolization device of FIG. 12.
Figure 14:
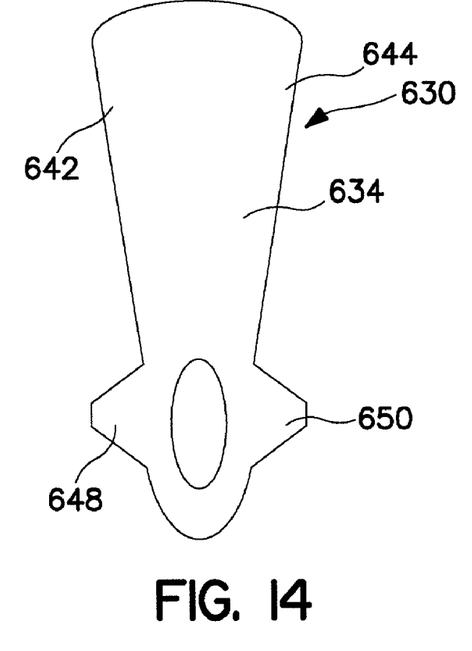
FIG. 14 is a schematic top view of the aerosolization device of FIG. 12 before being converted into its aerosolization configuration.
Figure 15:
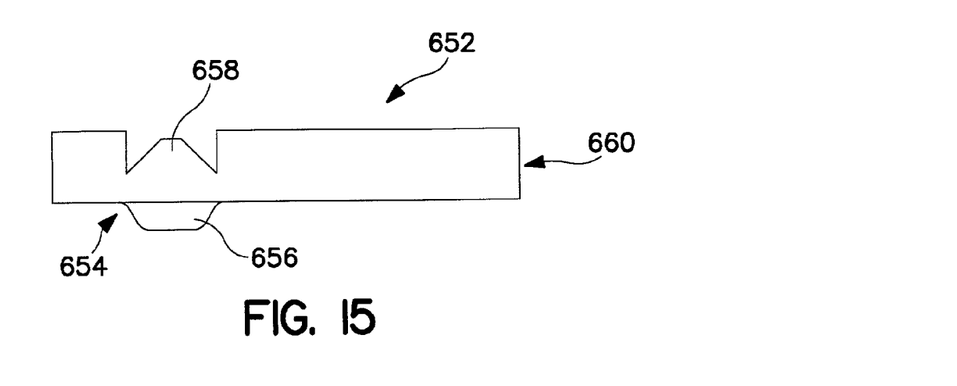
FIG. 15 is a schematic side view of another version of an aerosolization device.
Figure 16A:
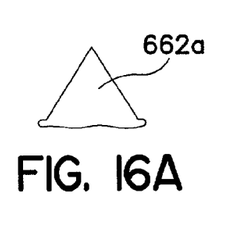
FIGS. 16A-16F illustrate various embodiments of piercing elements that may be used with an aerosolization device according to the invention.
Figure 16B:
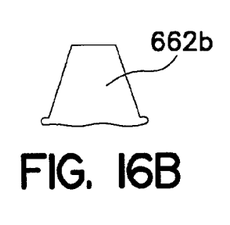
Figure 16C:
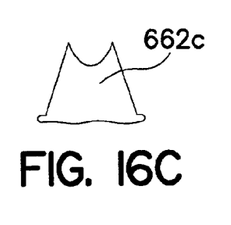
Figure 16D:
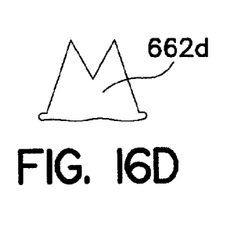
Figure 16E:
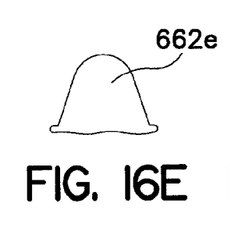
Figure 16F:
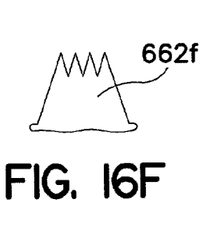
Figure 17A:
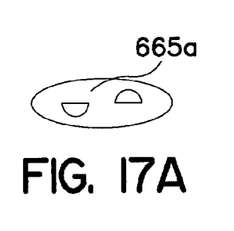
FIGS. 17A-17F illustrate various hole patterns that may be formed in the lid of a receptacle by piercing elements according to the invention.
Figure 17B:
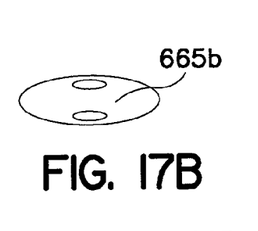
Figure 17C:
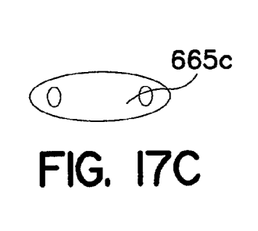
Figure 17D:
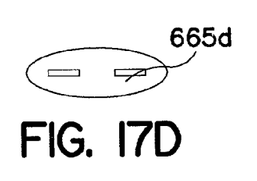
Figure 17E:
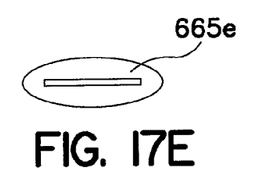
Figure 17F:
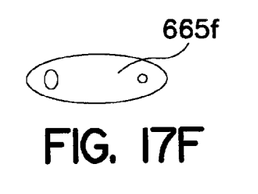
Figure 18A:
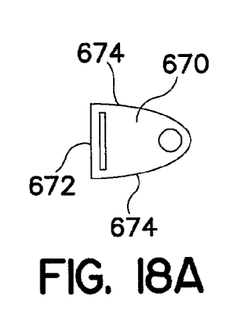
FIGS. 18A and 18B illustrate an alternative lid configuration and various hole patterns that may be formed in the lid by piercing elements according to the invention.
Figure 18B:
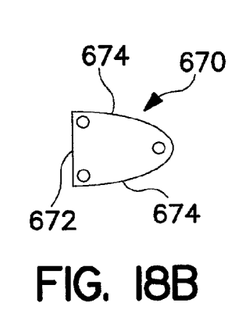
Figure 19:
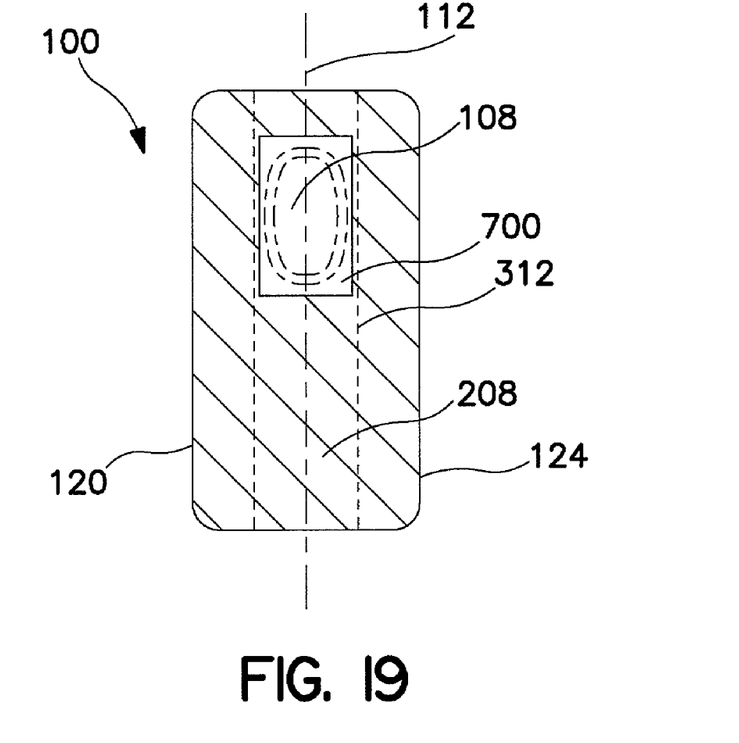
FIG. 19 is a schematic top view of another version of an aerosolization device.
Figure 20:
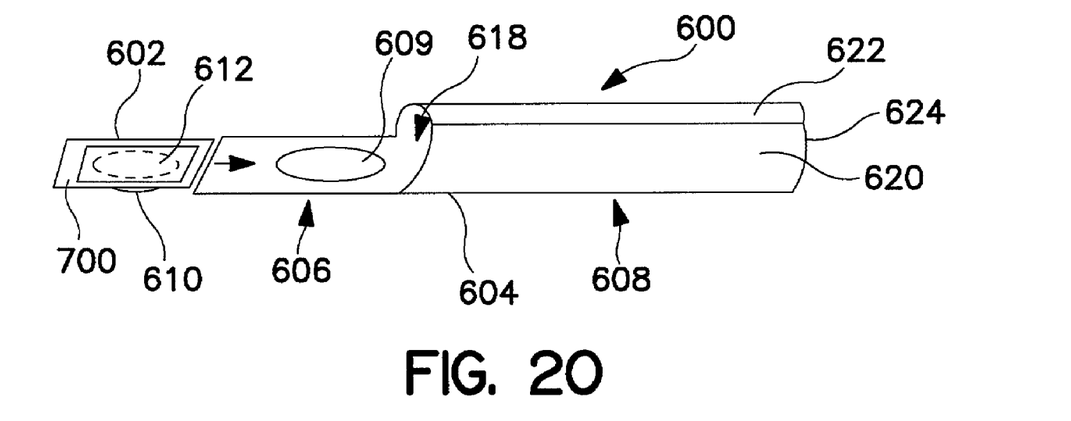
FIG. 20 is a schematic perspective view of another version of an aerosolization device.

As with all the embodiments described herein, conduit 618 may have a variety of shapes. In some embodiments, conduit 618 may be fashioned so that the gas stream flowing over lid 612 is maximized during inhalation to facilitate extraction of the powder. One example of such a configuration is illustrated in FIG. 11 where sides 620 and 622 have been formed so as to form a pair of conduits 626 and 628. These conduits serve to channel gas streams across lid 612 to facilitate aerosolization. Such an embodiment is particularly useful with the configuration of piercing elements 614 and 616 which provide access holes on opposing sides of chamber 610.

Another way to increase the gas flow over the receptacle is to taper the conduit in the direction of the receptacle. Such an example is illustrated in FIGS. 12 and 13. These figures illustrate an aerosolization device 630 that is configured to be used with a separate receptacle in a manner similar to that previously described in connection with device 600. However, it will be appreciated that device 630 could include an integrated receptacle similar to other embodiments. Device 630 comprises a device body 634 having a holding region 636 and a conduit region 638. Conduit region 638 includes a conduit 640 that is formed by rolling two sides 642 and 644 of device body 634. As best shown in FIG. 14, device body 634 is constructed so that sides 642 and 644 when rolled together form a tapered conduit. In this way, when the user inhales from an end 646, the gas flow is accelerated to increase the flow rate across the receptacle.

Aerosolization device 630 further includes a pair of piercing elements 648 and 650 that are configured to pierce holes within the receptacle lid in a manner similar to that previously described in connection with device 600. As shown, piercing elements 648 and 650 include a flat end rather than a pointed end as with device 600. In this way, an elongate slit is provided when the piercing elements are forced through the lid. As described in greater detail hereinafter, each of the inhalation devices described herein may be provided with a variety of piercing elements depending on the desired hole size and pattern that is to be produced within the receptacle lid.

In the embodiments of FIGS. 7 and 12, the piercing elements are generally spaced apart from the conduit to facilitate easy squeezing of the piercing elements to form the access holes. In some cases, the piercing elements may be provided within the conduit itself. One such example is illustrated in FIG. 15 where an aerosolization device 652 is shown. Aerosolization device 652 includes a holding region 654 having a depression 656 for holding a receptacle in a manner similar to other embodiments. Further, piercing elements 658 are positioned on either side of depression 656. A conduit 660 extends along the length of device 652, but only partially along holding region 654 as shown. This configuration permits piercing elements 658 to be squeezed through the lid of the receptacle in a manner similar to that described with other embodiments. As the same time, conduit 660 is formed along the length of the device to facilitate air flow across the receptacle lid when extracting and aerosolizing the powdered medicament.

As previously described, each of the inhalation devices described herein may employ a variety of piercing elements. Various non-limiting examples of such piercing elements are illustrated in FIGS. 16A-16F and are identified by reference numerals 662*a*-662*f*. For example, the piercing elements may have a single point 662*a*; a truncated region 662*b*; a double point 662*c*, 662*d*; a curved region 662*e*; and more than two points 662*f*. With each of the piercing elements, the edges may be sharpened or relatively thin to facilitate piercing of the receptacle lid. Further, it will be appreciated that each inhalation device may include one or more of the same and/or different piercing elements so that a variety of hole sizes and/or patterns may be produced.

Merely by way of example, some hole patters are illustrated in FIGS. 17A-17F. As shown, the hole sizes may be semi-circular, circular, oval, elongate, and the like. Further, the holes may be positioned at various locations in the receptacle lid. In some cases, the hole sizes may also be different within the same lid. For example, the holes may be longitudinally offset and semi-circular 665*a*; laterally offset and elongate 665*b*; longitudinally offset and laterally elongate 665*c*; longitudinally offset and longitudinally elongate 665*d*; singular 665*d*; and of different shapes 665*e*.

Further, it will be appreciated that the shape of the chamber may be varied to facilitate extraction of the powder. As shown in FIGS. 18A and 18B, a receptacle lid 670 has a straight edge 672 and two curved edges 674 to facilitate placement of different hole configurations and locations. Further, it will be appreciated that other chamber configurations may be produced as well as other hole shapes and/or sizes and/or locations to facilitate extraction of the powdered medicament.

In another version, the pharmaceutical formulation within the chamber 108, 602 may be accessed by means other than by piercing the lid. For example, as shown in the version of FIG. 19, the receptacle 108 may be covered by a lid 700 that may be peeled away from the chamber 108 to expose the pharmaceutical formulation within the chamber 108. Such peelable lids are commonly known in the art. The version of FIG. 19 is substantially the same as the version of the 3 but with the piercing elements replaced by the peelable lid 700. Similarly, as shown in FIG. 20, the piercing elements of the version shown in FIG. 7 can be replaced with a peelable lid 700 on the removably positionable blister package.

In a preferred version, the invention provides a system and method for aerosolizing a pharmaceutical formulation and delivering the pharmaceutical formulation to the lungs of the user. The pharmaceutical formulation may comprise powdered medicaments, liquid solutions or suspensions, and the like, and may include an active agent.

The active agent described herein includes an agent, drug, compound, composition of matter or mixture thereof which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized or systemic effect in a patient. An active agent for incorporation in the pharmaceutical formulation described herein may be an inorganic or an organic compound, including, without limitation, drugs which act on: the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable active agents may be selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally or systemically.

The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of active agents suitable for use in this invention include but are not limited to one or more of calcitonin, erythropoietin (EPO), Factor Vim, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., mono-acylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosponates, respiratory syncytial virus antibody, cystic fibrosis transmembrane regulator (CFTR) gene, deoxyreibonuclease (Dnase), bactericidal/permeability increasing protein (BPI), anti-CMV antibody, 13-cis retinoic acid, macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments and analogs thereof.

Active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense. Further, an active agent may comprise live attenuated or killed viruses suitable for use as vaccines. Other useful drugs include those listed within the Physician's Desk Reference (most recent edition).

The amount of active agent in the pharmaceutical formulation will be that amount necessary to deliver a therapeutically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1% by weight to about 99% by weight active agent, typically from about 2% to about 95% by weight active agent, and more typically from about 5% to 85% by weight active agent, and will also depend upon the relative amounts of additives contained in the composition. The compositions of the invention are particularly useful for active agents that are delivered in doses of from 0.001 mg/day to 100 mg/day, preferably in doses from 0.01 mg/day to 75 mg/day, and more preferably in doses from 0.10 mg/day to 50 mg/day. It is to be understood that more than one active agent may be incorporated into the formulations described herein and that the use of the term "agent" in no way excludes the use of two or more such agents.

The pharmaceutical formulation may comprise a pharmaceutically acceptable excipient or carrier which may be taken into the lungs with no significant adverse toxicological effects to the subject, and particularly to the lungs of the subject. In addition to the active agent, a pharmaceutical formulation may optionally include one or more pharmaceutical excipients which are suitable for pulmonary administration. These excipients, if present, are generally present in the composition in amounts ranging from about 0.01% to about 95% percent by weight, preferably from about 0.5 to about 80%, and more preferably from about 1 to about 60% by weight. Preferably, such excipients will, in part, serve to further improve the features of the active agent composition, for example by providing more efficient and reproducible delivery of the active agent, improving the handling characteristics of powders, such as flowability and consistency, and/or facilitating manufacturing and filling of unit dosage forms. In particular, excipient materials can often function to further improve the physical and chemical stability of the active agent, minimize the residual moisture content and hinder moisture uptake, and to enhance particle size, degree of aggregation, particle surface properties, such as rugosity, ease of inhalation, and the targeting of particles to the lung. One or more excipients may also be provided to serve as bulking agents when it is desired to reduce the concentration of active agent in the formulation.

Pharmaceutical excipients and additives useful in the present pharmaceutical formulation include but are not limited to amino acids, peptides, proteins, non-biological polymers, biological polymers, carbohydrates, such as sugars, derivatized sugars such as alditols, aldonic acids, esterified sugars, and sugar polymers, which may be present singly or in combination. Suitable excipients are those provided in WO 96/32096, which is incorporated herein by reference in its entirety. The excipient may have a glass transition temperatures (Tg) above about 35° C., preferably above about 40° C., more preferably above 45° C., most preferably above about 55° C.

Exemplary protein excipients include albumins such as human serum albumin (HSA), recombinant human albumin (rHA), gelatin, casein, hemoglobin, and the like. Suitable amino acids (outside of the dileucyl-peptides of the invention), which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, isoleucine, tryptophan, alanine, methionine, phenylalanine, tyrosine, histidine, and proline. Dispersibility-enhancing peptide excipients include dimers, trimers, tetramers, and pentamers comprising one or more hydrophobic amino acid components such as those described above.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like.

The pharmaceutical formulation may also include a buffer or a pH adjusting agent, typically a salt prepared from an organic acid or base. Representative buffers include organic acid salts of citric acid, ascorbic acid, gluconic acid, carbonic acid, tartaric acid, succinic acid, acetic acid, or phthalic acid, Tris, tromethamine hydrochloride, or phosphate buffers.

The pharmaceutical formulation may also include polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-β-cyclodextrin and sulfobutylether-β-cyclodextrin), polyethylene glycols, and pectin.

The pharmaceutical formulation may further include flavoring agents, taste-masking agents, inorganic salts (for example sodium chloride), antimicrobial agents (for example benzalkonium chloride), sweeteners, antioxidants, antistatic agents, surfactants (for example polysorbates such as "TWEEN 20" and "TWEEN 80"), sorbitan esters, lipids (for example phospholipids such as lecithin and other phosphatidylcholines, phosphatidylethanolamines), fatty acids and fatty esters, steroids (for example cholesterol), and chelating agents (for example EDTA, zinc and other such suitable cations). Other pharmaceutical excipients and/or additives suitable for use in the compositions according to the invention are listed in "Remington: The Science & Practice of Pharmacy", 19th ed., Williams & Williams, (1995), and in the "Physician's Desk Reference", 52nd ed., Medical Economics, Montvale, N.J. (1998), both of which are incorporated herein by reference in their entireties.

"Mass median diameter" or "MMD" is a measure of mean particle size, since the powders of the invention are generally polydisperse (i.e., consist of a range of particle sizes). MMD values as reported herein are determined by centrifugal sedimentation, although any number of commonly employed techniques can be used for measuring mean particle size. "Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, generally in air, as the particle. The aerodynamic diameter encompasses particle shape, density and physical size of a particle. As used herein, MMAD refers to the midpoint or median of the aerodynamic particle size distribution of an aerosolized powder determined by cascade impaction.

In one version, the powdered formulation for use in the present invention includes a dry powder having a particle size selected to permit penetration into the alveoli of the lungs, that is, preferably 10 μm mass median diameter (MMD), preferably less than 7.5 μm, and most preferably less than 5 μm, and usually being in the range of 0.1 μm to 5 μm in diameter. The delivered dose efficiency (DDE) of these powders may be greater than 30%, more preferably greater than 40%, more preferably greater than 50% and most preferably greater than 60% and the aerosol particle size distribution is about 1.0-5.0 μm mass median aerodynamic diameter (MMAD), usually 1.5-4.5 μm MMAD and preferably 1.5-4.0 μm MMAD. These dry powders have a moisture content below about 10% by weight, usually below about 5% by weight, and preferably below about 3% by weight. Such powders are described in WO 95/24183, WO 96/32149, WO 99/16419, and WO 99/16422, all of which are all incorporated herein by reference in their entireties.

Hence, the inhalers of the invention provide a number of significant advantages. For example, the invention takes advantage of the benefits offered by the pulmonary delivery of dry powdered drugs or vaccines and provides unique ways to accomplish the pulmonary delivery. The advantages of using powders over liquids include greater dispersion reaching distal (alveolar) regions of the lung, the ability to confer mucosal and systemic immunity, and the promising delivery of proteins and polypeptides. Further, powders have other advantages over liquid vaccines including the absence of cold-chain, simpler administration, lower transportation costs, lower likelihood of infection, and the absence of preservatives. In terms unique ways to accomplish pulmonary delivery, the invention in some embodiments maximizes the utilization of the packaging of the powdered medicament such that the packaging receptacle stores the unit dosage and inexpensively forms an inhaler that is used to administer it. This in turn lowers the cost of production, shipping and storage. In other embodiments, the inhalation device may be reused with relatively inexpensive receptacles.

While the principles of the invention have been described above in connection with specific apparatuses and methods, it is to be clearly understood that this description is made only by way of example and not as limitation on the scope of the invention.

What is claimed is:

1. An aerosolization device comprising:
   a chamber adapted to contain a powder pharmaceutical formulation;
   a lid at least partially covering the chamber;
   at least one piercing element forcible through the lid to provide access to the powder pharmaceutical formulation; and
   a shapeable surface extending from the chamber, the shapeable surface being adapted to undergo a shape change to form a conduit,
   whereby the powder pharmaceutical formulation may be extracted from the chamber by a user inhaling through the conduit.

2. An aerosolization device according to claim 1 wherein the shapeable surface is adapted to undergo a shape change in response to a force being applied thereto by the user.

3. An aerosolization device according to claim 1 wherein the shapeable surface is adapted to undergo a shape change in response to a force being applied thereto by the user.

4. An aerosolization device according to claim 1 wherein the shapeable surface includes means for encouraging the surface to form the conduit.

5. An aerosolization device according to claim 4 wherein the means for encouraging comprises one or more perforations.

6. An aerosolization device according to claim 1 wherein the surface is substantially flat before undergoing the shape change.

7. An aerosolization device according to claim 1 wherein the chamber is an integral portion of the shapeable surface.

8. An aerosolization device according to claim 1 wherein the chamber is a cavity formed in the shapeable surface.

9. An aerosolization device according to claim 1 wherein the chamber is formed in a surface that is removably positionable on the shapeable surface.

10. An aerosolization device according to claim 1 wherein the piercing element is an integral portion of the shapeable surface.

11. An aerosolization device according to claim 1 wherein the piercing element and the shapeable surface are one-piece.

12. An aerosolization device according to claim 1 wherein at least a portion of the piercing element is connected to the shapeable surface by a perforated portion of the shapeable surface.

13. An aerosolization device according to claim 1 wherein the piercing element comprises a pointed tab formed from the shapeable surface.

14. An aerosolization device according to claim 13 wherein the piercing element is located adjacent to the chamber and is bendable to permit the pointed tab to pierce the lid.

15. An aerosolization device according to claim 1 wherein the shapeable surface has a longitudinal axis and wherein two sides of the shapeable surface that lie on opposing sides of the longitudinal axis are bendable towards each other to form the conduit.

16. An aerosolization device according to claim 1 wherein the lid comprises a foil.

17. An aerosolization device according to claim 1 wherein the lid, the piercing element and the shapeable surface lie in a common plane prior to piercing of the lid and the formation of the conduit.

* * * * *